United States Patent [19]

Cerwin

[11] 4,014,433
[45] Mar. 29, 1977

[54] PACKAGE FOR MOISTURE SENSITIVE SUTURES AND METHOD FOR MAKING SAME

[75] Inventor: Robert J. Cerwin, Pittstown, N.J.

[73] Assignee: Ethican, Inc., Somerville, N.J.

[22] Filed: May 27, 1975

[21] Appl. No.: 581,057

[52] U.S. Cl. .................................. 206/63.3; 53/29; 156/309; 206/484

[51] Int. Cl.² ......................................... A61L 17/02

[58] Field of Search ................ 53/39, 42, 329, 341; 156/309; 206/63.3, 84, 438, 527, 484, 811, 819; 229/3.5 R, 3.5 MF, 48 T

[56] References Cited

UNITED STATES PATENTS

| | | | |
|---|---|---|---|
| 2,993,589 | 7/1961 | Zoller et al. | 206/63.3 |
| 3,221,873 | 12/1965 | Bowes et al. | 206/63.3 |
| 3,815,315 | 6/1974 | Glick | 206/63.3 |

Primary Examiner—Steven E. Lipman
Attorney, Agent, or Firm—Wayne R. Eberhardt

[57] ABSTRACT

A laminated package comprising two panels of a moisture impervious material such as aluminum foil coated on adjacent interior surfaces with a heat sealable resin such as polypropylene, and peripherally heat sealed at the edge margins with a continuous and substantially bubble free seal to enclose a moisture sensitive suture within the package. The package is highly resistant to penetration by water vapor, and moisture sensitive sutures thus packaged are well protected against degradation by atmospheric moisture diffusing into the package through the heat seal layer during storage.

26 Claims, 5 Drawing Figures

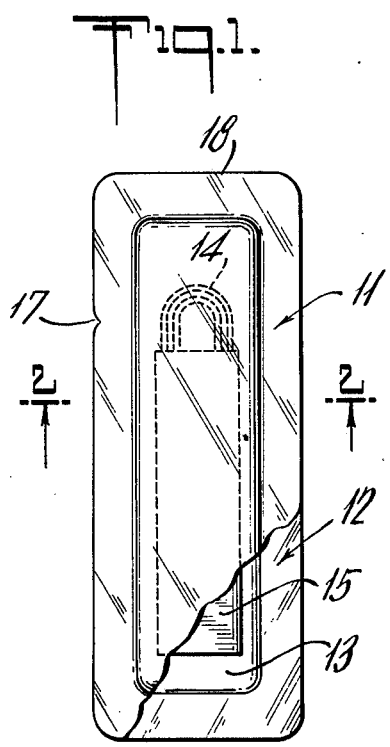
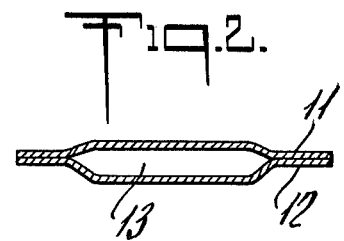
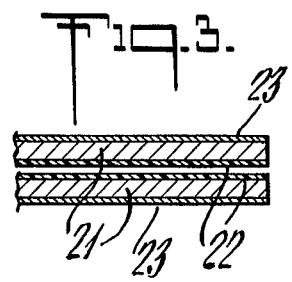
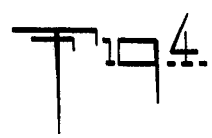
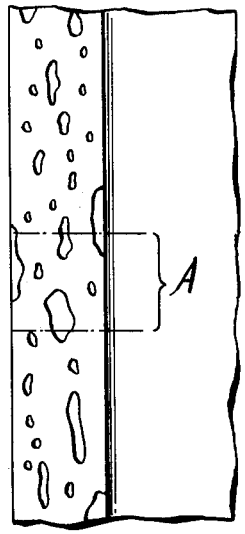
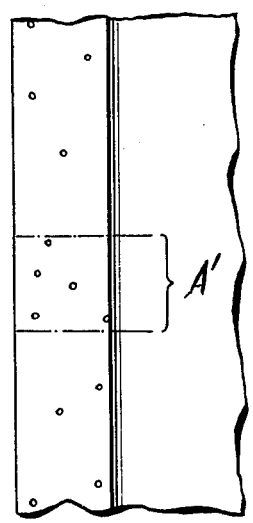

PACKAGE FOR MOISTURE SENSITIVE SUTURES AND METHOD FOR MAKING SAME

BACKGROUND OF INVENTION

1. Field of the Invention

This invention relates to suture packages and more particularly to moisture permeation resistant packages for moisture sensitive suture materials.

2. Description of Prior Art

Heat sealed laminated packages have been used to package sterile sutures for a number of years. The packages are hermetically sealed to provide a perfect barrier against the transmission of bacteria and microorganisms and preserve the sterility of the suture contained therein indefinitely.

A commonly used package construction is one comprising an outside layer of aluminum foil and an inside layer of a thermoplastic heat sealable material. The aluminum may additionally be covered with a paper or plastic film to reinforce and protect the metal from corrosion and/or to provide a label on the package.

Synthetic absorbable sutures such as homopolymers and copolymers of lactide and glycolide are known to be susceptible to hydrolytic degradation by even minute amounts of water vapor. Great care is accordingly taken during packaging to remove substantially all traces of moisture from the suture and the interior of the package in order to seal the suture in a substantially anhydrous environment. Conventional laminated packages however, while providing a perfect barrier against biological contamination of the suture, have been discovered to provide less than adequate protection against permeation by water vapor. When a conventional package is stored for extended periods of time under condition of ambient temperature and humidity, a significant amount of water vapor is characteristically able to diffuse into the package through the heat seal layer to attack and degrade the moisture sensitive suture material.

It is accordingly an object of the present invention to provide an improved package for moisture sensitive sutures. It is a further object of this invention to provide a metal foil/polymeric film laminate package having great resistance to penetration by water vapor. It is another object of this invention to provide a method whereby the resistance to water vapor permeation of laminate packages constructed of conventional materials may be improved. Yet other objects of this invention will be apparent from the ensuing description and claims.

SUMMARY

In accordance with the present invention, the resistance to water vapor permeability of laminated and heat sealed suture packages is significantly improved by providing the package with a heat seal characterized by a substantial absence of bubbles within the seal area. Continuous and substantially bubble free seals in combination with metal foil of sufficient thickness to eliminate or minimize the existence of pinholes, and a heat sealable polymeric film having inherently high resistance to water vapor transmission, provide a suture package which is substantially impervious to penetration by water vapor.

DESCRIPTION OF DRAWING

FIG. 1 is a partially broken away plan view of a representative laminated sterile suture package.

FIG. 2 is a cross-sectional view of the package of FIG. 1 taken along the line 2—2 of FIG. 1 with the enclosed suture omitted for clarity.

FIG. 3 is a greatly enlarged sectional view of the laminates forming the top and bottom panels of the package before heat sealing.

FIG. 4 is a greatly enlarged transparent view of a section of a conventional seal area illustrating bubbles within the seal area. FIG. 5 is a greatly enlarged transparent view of a section of a substantially bubble free seal area in accordance with the present invention.

DESCRIPTION OF PREFERRED EMBODIMENTS

FIG. 1 illustrates a representative suture package comprising a top panel 11 and a bottom panel 12 which are superimposed and sealed to one another along their edge margins to completely enclose and hermetically seal off central space 13. A coiled sterile surgical suture 14 inside a paper sleeve 15 is enclosed within central space 13. A tearing notch 17 is located adjacent one end 18 of the package along its top edge to permit the package to be opened by tearing from notch 17 to the opposite side of the package.

The package is of a laminated construction as illustrated in FIG. 2 and FIG. 3. Both top and bottom panels consist of a metal foil layer 21 coated on the inner surface thereof with a heat sealable polymer layer 22. In addition, the outer surface of the metal foil is covered with paper or plastic layer 23 to reinforce and protect the metal layer during handling and to provide a printing surface for the package label. In the assembly of the package, the top and bottom panels are placed together and sealed by the application of heat and pressure to unify plastic layers 22 and form a single layer in the seal area. Conventional heat seals characteristically contain a significant proportion of bubbles within the borders of the seal as illustrated in FIG. 4, and the presence of these bubbles has now been discovered to increase the rate of water vapor transmission through the seal area. It has further been discovered that by providing the package with seals that are substantially bubble free as illustrated in FIG. 5, the resistance of the suture package to permeation by water vapor is significantly increased.

The extent to which a seal is free of bubbles is defined as "seal integrity", a high seal integrity indicating a relatively low proportion of bubble area, and a low seal integrity indicating a higher proportion of bubble area. A numerical value for seal integrity is obtained by comparing the area of bubbles relative to total seal area according to the following relationship:

$$\text{Seal Integrity (\%)} = \left(1 - \frac{\text{bubble area}}{\text{seal area}}\right) \times 100$$

The suture packages of the present invention are best characterized in terms of square seal integrity which is defined as the seal integrity of a square increment of the seal. In determining "minimum square seal integrity" for a given package, the seal integrity is determined for that square portion of the seal containing the highest relative bubble area. Determination of square seal integrity is illustrated in FIGS. 4 and 5 where square seal areas A and A' respectively each contain the highest relative bubble area in their respective seals.

The determination of square seal integrity has the advantage of reflecting bubble distribution and is in effect a measurement of the weakest section of the seal. A seal having a high overall seal integrity may nevertheless provide poor protection against water vapor permeation if the total bubble area is concentrated in a small area of the seal. Square seal integrity highlights weak seal areas and provides a reliable indication of the actual permeation resistance of the suture package.

Seal integrity of a metal laminated package may be determined by chemically stripping the metal foil from the package to reveal the transparent film, and then simply measuring the bubble area in any selected area of the seal. Aluminum foil packages, for example, are readily stripped of the metal by immersing the package in a solution of about 6N hydrochloric acid for about 15 to 30 minutes at room temperature. Measurement of bubble area in a selected area of the seal is facilitated by placing that portion of the seal including the area to be measured in a photographic enlarger and printing an enlarged image in which the bubbles are readily visible. Measurements can then readily be made from the photograph over any selected square seal area.

The improved suture packages of the present invention are characterized by a seal which is continuous around the perimeter of the package, and wherein the minimum square seal integrity of the seal is not less than about 90 percent. Such seals are defined as being "substantially bubble free". Most preferably, minimum square seal integrity is from 95 to 100 percent for maximum resistance to water vapor permeation.

The effect of square seal integrity on water vapor permeability through the seal was demonstrated by direct comparison testing of suture packages having conventional and bubble free seals. In each instance, test packages were constructed of an aluminum foil/polymer film laminate. Heat sealable polymers evaluated in the test included polyvinyl chloride, polypropylene, and Surylyn A, a DuPont ionomer resin which is an ionic cross-linked ethylene-acrylic copolymer containing metal ions. Ionomer resins are described in *Modern Packaging*, pp 157–161, May 1967 and pp 173–175, June 1967.

In the following examples, water vapor permeability was determined by sealing one milliliter of tritiated water equal to 0.01 curie inside each package. The sealed packages were hung in individual glass jars with a vial of anhydrous glycerol and maintained at 37° C. The glycerol vials were replaced at weekly intervals, and the amount of tritiated water which permeated out of the package and became hydrated with the glycerol during each week was determined using liquid scintillation counting. The method allowed the water permeation rate to be followed over a period of several weeks without disturbing the test packages. Since the packages were identical except for polymer composition ad seal integrity, differences in water permeation rates were directly relatable to these variables. The data obtained over a 10 week test period are presented in TABLE I. Minimum square seal bubble integrity of each package in TABLE I was objectively determined using a Quantimet 720 Image Analyzing Computer manufactured by IMANCO, Monsey, N.Y. The test packages were stripped of metal foil and photographic prints made of the heat seal areas as above described. The photographs were placed in the Epidiascope attachment of the image analyzer and the square seal area containing the highest proportion of bubble area selected and displayed on the visual scope of the instrument for analysis by the computer.

TABLE I

| Package | SSI | Package Permeation, Micrograms of Water Per Week | | | | | | | 10 week cumulative permeation |
|---|---|---|---|---|---|---|---|---|---|
| | | 1st wk. | 2nd wk | 3rd wk | 4th wk | 5th wk | 6th wk | 7–10 wks | |
| A. Polyvinyl chloride | | | | | | | | | |
| conventional seal | 80 | 0.05 | 0.53 | 1.31 | 1.71 | 1.88 | 2.22 | 9.94 | 17.64 |
| bubble free seal | 90 | .04 | .04 | .11 | .29 | .55 | .56 | 5.64 | 7.53 |
| B. Ionomer | | | | | | | | | |
| conventional seal | 32 | 0.09 | 0.17 | 0.28 | 0.36 | 0.39 | 0.59 | 2.34 | 4.22 |
| bubble free seal | 100 | .05 | .04 | .05 | .04 | .05 | .05 | .09 | .37 |
| C. Polypropylene | | | | | | | | | |
| bubble free seal (a) | 93 | 0.06 | 0.09 | 0.38 | 0.73 | 0.93 | 1.09 | 5.93 | 9.21 |
| bubble free seal (b) | 100 | .04 | .05 | .14 | .33 | .58 | .70 | 4.07 | 5.91 |

SSI = Square Seal Integrity

It is apparent from the data in TABLE I that in packages A and B, the bubble free seal allowed significantly less water vapor permeation through the seal than did the conventional seal. Package C illustrates that even within the bubble free seal range, higher values of square seal integrity of from 95 to 100 percent are preferred to minimize water vapor permeability of the package. The data in TABLE I also illustrates inate differences between polymer types in water vapor permeability, and that a bubble free ionomer seal has exceptional resistance to water vapor transmission.

All of the above tests involved rectangular packages 3⅞ × 1⅜ inches (9.8 × 3.5 cm) having a seal width of ⅜ inch (0.95 cm) on three sides and ¼ inch (0.63 cm) on one long side. The aluminum foil was 1.35 mils (0.035 mm) thick in the top panel, 2.0 mils (0.051 mm) thick in the bottom panel and nominally pinhole free. The polymer film was about 1.0 mil (0.025 mm) thick in each package and continuous over the entire inner surface of the aluminum foil. The packages were heat sealed to give a seal peal strength of at least 2 pounds per inch (357 g/cm).

In a preferred embodiment of the present invention, the minimum width of the seal is greater than about ⅛ inch (0.32 cm), and most preferably from about 5/32 to ½ inch (0.40 to 1.27 cm) to minimize water vapor permeation. The aluminum foil is preferably at least 1 mil (0.025 mm) thick, and most preferably from 1.25 to 2.0 mils (0.032 to 0.051 mm) thick in order to eliminate or minimize the incidence of pinholes. The heat sealing polymeric layer on the other hand, is preferably kept to a minimum thickness to reduce the edge thickness and area through which water vapor may penetrate the package. Preferred polymer film thickness is from about 0.25 to 1.5 mils (0.0064 to 0.038 mm) although even thinner films may be used in some instances. A particularly preferred suture package of the present invention is a package comprising a laminate of aluminum foil and ionomer resin of a preferred thickness and having a substantially bubble free seal as illustrated by package B of TABLE I.

Conventional suture packages are characterized by a high incidence of bubbles in the seal area, often the result of sealing by compression between two flat dies with the resulting entrapment of bubbles. The bubble free seals of the present invention may be obtained by using rolling or crowned dies which provide moving line sealing to the exclusion of bubbles. The present invention however, is not limited to any particular method of sealing and any convenient method which yields a bubble free seal may be used.

While the aforedescribed water permeation test involves the diffusion of water vapor through the package from the inside to the outside, there is of course no significance to the direction of permeation. In the case of a sterile suture package where substantially all water has been removed from the inside of the package, the ambient moisture in the atmosphere surrounding the package provides the driving force for diffusion of water to the area of lower concentration inside the package.

Moisture diffusion rates into a conventional suture package for a synthetic absorbable suture of polyglycolic acid was determined by sealing individual suture packages in aluminum foil/ionomer film laminate pouches containing 1 ml of tritiated water equal to 0.01 curie. The sealed pouches were stored at 37° C. After 16 weeks, the pouches were opened and the suture packages removed and decontaminated. The packages were then opened and the paper folder and suture combusted in a Packard Sample Oxidizer. The products of combustion were collected and read in a liquid scintillation counter to determine the quantity of moisture which had permeated into the package. The procedure was repeated with suture packages having a substantially bubble free seal and preferred seal widths, aluminum foil thickness and polymer film thickness in accordance with the present invention. Package descriptions and water vapor permeation rates are presented in TABLE II below.

tures which do not affect considerations of seal integrity as described herein. The packages may also be formed of multi-layer laminates having layers of metal, plastic, paper and functional or decorative coatings, all in addition to the basic metal foil and heat sealable film of the laminates described herein. Metals other than aluminum, may also be used although aluminum is highly preferred for reasons of economy and availability.

Heat sealable thermoplastic polymers other than those illustrated in the examples may be used with good results. Representative examples of such thermoplastic polymers include other aliphatic polyolefins such as polyethylene, aromatic polyolefins such as styrene, other halogenated polyolefins such as polyvinylidene chloride, other carboxylated polyolefins such as polyacrylates and polyvinyl acetates, hydroxylated polyols such as polyvinyl alcohol, cellulosics, polyurethanes, polyamides, polyesters, polycarbonates, polyethers, and acrylics, and various combinations of the above as copolymers, polymer blends and composite film laminates. Particularly preferred polymers are polypropylene, polyvinylchloride, polyvinylidene chloride, and ionomer.

The suture package may be laminated from two separate panels or formed by folding a single sheet of polymer coated aluminum so that only three sides are required to be heat sealed. The suture package may itself be packaged in a sterile or non-sterile overwrap which may or may not provide an additional barrier against water vapor permeability into the suture package. These and other variations are included within the scope of the present invention which is not to be limited except as defined by the following claims.

What is claimed is:

1. A substantially water vapor impervious package for moisture sensitive materials comprising two panels of a water vapor impermeable material coated on at least the edge margins of adjacent interior surfaces with a heat sealable polymer, said panels being joined through said edge margins about the periphery of said package by a continuous seal to enclose the moisture sensitive material within the central space of said package, said seal being characterized by having a square seal integrity of at least about 90 percent.

2. A package of claim 1 wherein said water vapor

TABLE II

| Suture Package | Aluminum Foil Thickness (Top) | (Bottom) | Polymer Film Type | Thickness | Seal Width | Moisture Permeation Micrograms A₂O |
| --- | --- | --- | --- | --- | --- | --- |
| Conventional | 1.3 (0.033, | 1.3 mils (0.033 mm) | Polyethylene | 1.1 mils (0.028 mm) | 1/8 – 3/16 in. (0.32 – 0.48 cm) | 5,958 (16 weeks) |
| This Invention | 1.35, (0.034, | 2.0 mils (0.050 mm) | Polyvinylchloride | 0.5 mils (0.013 mm) | 9/32 – 3/8 in. (0.71 – 0.95 cm) | 41.6 (24 weeks) |

Since it is known that moisture either sealed in the package with the suture or subsequently entering the package after sealing has an adverse effect upon the storage stability of the suture, the present invention includes a method for improving the storage stability of a moisture sensitive suture by providing a suture package having a high seal integrity and high resistance to moisture permeation as described herein.

Many variations in the improved method and suture package of the present invention will be apparent to those skilled in the art. The package may for example, be formed in various shapes and sizes with design feaimpermeable material is metal foil.

3. A package of claim 2 wherein said metal foil is aluminum foil.

4. A package of claim 3 wherein the aluminum foil is at least about 1.0 mil thick.

5. A package of claim 1 wherein the heat sealable polymer coating has a thickness of from about 0.25 to 1.5 mils.

6. A package of claim 1 wherein the heat sealable polymer is a polyolefin.

7. A package of claim 1 wherein the heat sealable polymer is polyvinyl chloride.

8. A package of claim 1 wherein the heat sealable polymer is polyvinylidene chloride.

9. A package of claim 1 wherein the heat sealable polymer is ionomer.

10. A package of claim 1 wherein the width of the seal is greater than about 1/8 inch.

11. A package of claim 1 wherein the moisture sensitive material is a surgical suture.

12. A substantially water vapor impervious package for moisture sensitive suture materials comprising two panels of water vapor impermeable metal foil coated on at least the edge margins of adjacent interior surfaces with a heat sealable polymer, said panels being joined through said edge margins about the periphery of said package by a continuous seal to enclose the moisture sensitive suture material within the central space of said package, said seal being characterized by a square seal integrity of 95 to 100 percent.

13. A package of claim 12 wherein said metal foil is aluminum foil having a thickness of at least about 1.0 mil.

14. A package of claim 12 wherein the minimum width of the seal is greater than about 1/8 inch.

15. A package of claim 12 wherein the moisture sensitive suture material is a homopolymer or copolymer of lactide and glycolide.

16. A package of claim 15 wherein the aluminum foil has a thickness of from about 1.25 to 2.0 mils.

17. A package of claim 16 wherein the minimum width of the seal is between about 5/32 and 1/2 inch.

18. A package of claim 17 wherein the heat sealable polymer is ionomer.

19. A package of claim 17 wherein the heat sealable polymer is polyvinyl chloride.

20. In a method for packaging moisture sensitive suture materials by enclosing said suture material in a hermetically sealed package formed by two panels of metal foil coated on at least the end margins of adjacent interior surfaces with a heat sealable polymer, said panels being joined through said heat sealable polymer in a continuous seal around the periphery of said panels to enclose the moisture sensitive suture material in the central space thereof, the improvement comprising increasing the storage stability of said suture material by sealing said package with a seal having a square seal integrity of at least about 90 percent.

21. A method of claim 20 wherein the minimum width of the seal is greater than about 1/8 inch.

22. A method of claim 20 wherein the minimum width of the seal is between about 5/32 and 1/2 inch.

23. A method of claim 22 wherein the seal has a square seal integrity of 95 to 100 percent.

24. A method of claim 20 wherein the suture material is a homopolymer or copolymer of lactide and glycolide.

25. A method of claim 20 wherein the heat sealable polymer is ionomer.

26. A method of claim 20 wherein the heat sealable polymer is polyvinyl chloride.

* * * * *

UNITED STATES PATENT AND TRADEMARK OFFICE
CERTIFICATE OF CORRECTION

PATENT NO. : 4,014,433
DATED : March 29, 1977
INVENTOR(S) : Cerwin, Robert J.

It is certified that error appears in the above-identified patent and that said Letters Patent are hereby corrected as shown below:

On front page of patent, the word "ETHICAN" should read --- ETHICON ---.

In Column 2, line 63, the word square seal integrity should read ---"square seal integrity"---.

In Column 4, line 6, the word "ad" should read --- and ---.

Signed and Sealed this

Twentieth Day of September 1977

[SEAL]

Attest:

RUTH C. MASON
Attesting Officer

LUTRELLE F. PARKER
Acting Commissioner of Patents and Trademarks